| United States Patent [19] | [11] 4,021,303 |
|---|---|
| Nakabayashi | [45] May 3, 1977 |

[54] METHOD FOR TREATMENT OF MICROORGANISMS

[75] Inventor: Yutaka Nakabayashi, Fukuoka, Japan

[73] Assignee: Dai-Nippon Sugar Manufacturing Co., Ltd., Tokyo, Japan

[22] Filed: Dec. 30, 1975

[21] Appl. No.: 645,505

Related U.S. Application Data

[63] Continuation-in-part of Ser. No. 414,576, Nov. 9, 1973, abandoned.

[30] Foreign Application Priority Data

Nov. 10, 1972 Japan .............................. 47-112026
Nov. 10, 1972 Japan .............................. 47-112027

[52] U.S. Cl. .................................. 195/5; 426/656; 260/112 R
[51] Int. Cl.² .......................................... A23J 3/00
[58] Field of Search ............ 426/60, 656, 431, 478; 195/4, 5, 28 N, 105; 260/112 R

[56] References Cited

UNITED STATES PATENTS

| 3,585,179 | 6/1971 | Samejima et al. ............. 260/112 R |
| 3,686,144 | 8/1972 | Tamura et al. ................ 426/656 X |
| 3,725,075 | 4/1973 | Muroi et al. .................. 260/112 R |
| 3,775,393 | 11/1973 | Akin et al. ....................... 195/28 N |
| 3,781,264 | 12/1973 | Akin .............................. 260/112 R |
| 3,821,080 | 6/1974 | Kalina et al. .......................... 195/5 |

*Primary Examiner*—Raymond N. Jones
*Assistant Examiner*—R. A. Yoncoskie
*Attorney, Agent, or Firm*—Sughrue, Rothwell, Mion, Zinn & Macpeak

[57] ABSTRACT

Microorganisms are chemically treated with alkali at a pH of 10.5 – 12.9 and a temperature of 0° – 30° C, washed with water and mechanically ruptured at a pH of 7 – 10.2.

7 Claims, No Drawings

METHOD FOR TREATMENT OF MICROORGANISMS

This application is a continuation-in-part application of Ser. No. 414,576, filed Nov. 9, 1973 and now abandoned.

BACKGROUND OF THE INVENTION

1. Field of the Invention

This invention relates to a method for the treatment of microorganisms. More particularly, this invention relates to a method for the treatment of microorganisms which comprises subjecting the cell membrane of microorganisms to at least one chemical treatment with an acid, an alkali or a hydrophilic solvent prior to the mechanical rupturing of the cell membrane thereby making the cell membrane fragile and, with or without isolation of the thus treated cells, mechanically rupturing the cell membrane using a sand grinder or a three roll mill. The present invention aims at the improvement in the processability and digestability of the microorganisms and the removal of unpleasant odors inherent in yeasts by releasing or eluting proteins or other intracellular substances outside the cells.

2. Description of the Prior Art

At present, the proteins produced by certain microorganisms are considered to be the most promising means for solving the shortage of proteins in the world, and such microorganisms are generally cultured in a medium comprising a carbon source such as saccharides, hydrocarbons, alcohols, carbon dioxide and the like, a nitrogen source such as ammonia, nitric acid, urea and the like, as predominant components together with the requisite minerals and vitamins. The microorganisms which are known to produce proteins efficiently include yeasts, bacteria, green algae, blue-green algae and the like. However, these microorganisms usualy have a tough cell membrane and, therefore, it is very difficult to fully utilize the characteristics of the proteins since the enzymatic lysis of cells is extremely low and the foodstuffs produced from the cells containing such proteins, for example, a textured protein, an imitation milk or reformed products thereof in which a wheat flour, a corn flour, etc. is incorporated, generally tend to isolate the original mono-cellular microorganism when such foodstuffs are mixed into water.

In order to eliminate these disadvantages, various methods have hithertofore been proposed, for example, an alkali extraction method for extracting proteins from the microorganism at a pH higher than about 13 and at a temperature of 45° to 65° C or more, or a cell membrane lysis method. However, these conventional methods tend to decrease the molecular weight of the proteins thereby reducing the usefulness of the proteins, and in addition the proteins obtained by these conventional methods lack good processability. Mechanical rupture of cells by an appropriate machine to extract enzymes has also been proposed, but, in this procedure, the rupture is not efficient and requires a prolonged time thereby resulting in the decomposition and/or denaturation of the proteins due to an endoenzyme present in the microorganisms. For such reasons, mechanical rupture has not yet been practically utilized in the industrial production of proteins from microorganisms.

SUMMARY OF THE INVENTION

A primary object of this invention is therefore to provide a method for the treatment of microorganisms which comprises chemically treating the microorganisms with an acid, an alkali or a hydrophilic solvent and thereafter mechanically rupturing the cell membrane of the resulting chemically treated microorganisms.

DETAILED DESCRIPTION OF THE INVENTION

As a result of extensive research for an efficient method for mechanically rupturing the cell membrane, it has been found that a raw material retaining a glutinous property, having excellent water solubility or dispersibility and having heat coagulating properties and yet having characteristic features of proteins of microorganisms with a less denaturation can be obtained by a combination of chemical and mechanical treatment of the cell membrane.

The object of this invention can be attained by first producing microorganisms containing fresh proteins, i.e., essentially natural proteins. The microorganisms which can be used in the present invention include broadly yeast, bacteria, algae and molds, but, from the standpoint of the use in foodstuffs, *Candida utilis, Saccharomyces cerevisciae, Saccharomyces fragilis* and *Saccharomyces carlsbergensis* are preferred since these microorganisms are known to be useful as foodstuffs. Also, *Lactobacillus burgaricus, Bacillus subtilis, Saccharomyces mise,* Chlorella or Senedesumus, or the like has been utilized in the foodstuff industry in Japan and can be used in the present invention. Other examples of the microorganisms which can be used in the present invention are photosynthetic microorganisms, for example, Spirulina or Arthrospirulina. These microorganisms can be cultured by various cultivation methods well established in the fermentation field and are now available in large quantities. It is well known that, since the above edible microorganisms are surrounded by a tough cell membrane, mere drying of the cells usually results in poor digestability of the cells and such dried cells usually does not possess the properties of processed proteins when the dried cells are used in foodstuffs as a protein raw material.

The present inventor found that the rupture ratio of the cell membrane of microorganisms can be increased when the microorganisms are chemically treated and then mechanically ruptured as compared with those which are not subjected to the chemical treatment. The following Reference Example was conducted on a fresh yeast, *Candida utilis,* which is aerobically cultured in a medium containing waste molasses as a carbon source In this experiment, the living cells are first subjected to various chemical treatments contemplated in the present invention and then mechanically ruptured using a laboratory scale homogenizer, i.e., Brawn Cell Homogeniser MSK Type 2876 (available from B. Brown Apparatebau Malaunger, Germany) where a large quantity of glass beads having a grain size of 0.2 to 2.5 mm is moved at a high speed, and the results obtained are compared with those obtained by the same procedure but using cells which have not been chemically treated.

Unless otherwise indicated, all percents and parts used herein are by weight.

REFERENCE EXAMPLE

A 10% aqueous slurry (based on the weight of the dried cells) of the yeast was subjected to a chemical treatment as described hereinafter to prepare samples. One of the samples was adjusted to a pH of 8.5 with ammonia, and toluene was added thereto in an amount of 2% and the resulting slurry was autolyzed at a temperature of 55° C for 2 hours to prepare Sample A. In the same manner, Samples B, C, D and E were prepared as follows: A portion of the slurry was adjusted to a pH of 12.4 with sodium hydroxide followed by stirring at 20° C for 1 hour (Sample B); a portion of the slurry was adjusted to a pH of 2.0 with hydrochloric acid followed by stirring at 50° C for 1 hour and finally adjusted to a pH of 4.0 with sodium hydroxide (Sample C); a filter cake (71% water content) obtained from the slurry was thoroughly comminuted in a mortar while adding ethanol in a volume equal to 10 times the volume of the filter cake followed by incubation at 43° C for 20 minutes. The cell is then separated, dried and slurried in water to make a 10% aqueous slurry (Sample D); and a 10% aqueous slurry (based on the weight of the dried cells) (Sample E). The cells contained in each of the Samples prepared above were then ruptured using a Brown Cell Homogeniser in a 50 cc glass vessel containing 25 cc of glass beads having an average grain size of 0.5 mm at an rpm rate of 3200 for 5 minutes while moving eccentrically. The ruptured samples were then microscopically observed (x 400) and the rupture ratio was found to be 87% in Sample A, 83% in Sample B, 83% in Sample C, 78% in Sample D and 62% in Sample E (Control). The "rupture ratio" used throughout the specification and claims is determined by microscopically counting the number of cells before and after the mechanical rupturing and is represented in terms of percent by the following:

$$\frac{\text{number of cells ruptured}}{\text{number of cells prior to rupturing}} \times 100$$

A further experiment was conducted on the above Samples to determine the properties of proteins free from ruptured cell membranes. The ruptured Samples A, B, C, D and E were made alkaline to a pH higher than 10 with sodium hydroxide at a temperature of 20° C followed by stirring for 20 minutes. The precipitated proteins were collected by centrifugation, washed twice with cold water each in a volume of 5 times the volume of the proteins, and the resulting protein portion was dissolved in a small amount of aqueous ammonia and sucrose was added to the solution in an amount of 5% based on the weight of the dried proteins. The solution was spread on an aluminum foil as a thin film and dried with hot air (about 40° C) to prepare Protein Samples P-A, P-B, P-C, P-D and P-E, respectively. As a control, a 20% aqueous slurry (based on the dried yeast) of the same yeast was combined with an equal volume of 1N sodium hydroxide followed by stirring for 3 hours at a temperature of 50° C. The mixture was adjusted to a pH of 7.5 with 6N HCl and centrifuged to remove the ruptured cell membrane, and the supernatant was adjusted to a pH of 4.0 to precipitate the proteins which were then washed with water, dissolved in aqueous ammonia and dried in the same manner as described above to prepare Protein-Sample P-F. The glutinous property, heat-coagulating property and nucleic acid content in the dry matter were then determined in each of the Protein-Samples and the results obtained are shown in Table 1.

Table 1

| Samples | P-A | P-B | P-C | P-D | P-E | P-F |
|---|---|---|---|---|---|---|
| Glutinous Property | ++++ | +++ | +++ | +++ | ++ | + |
| Heat-Coagulating Property | ++ | ++ | + | + | + | — |
| Nucleic Acid Content | 0.5% | 2.8% | 1.1% | 9.6% | 8.7% | 0.2% |

In the above determinations, the glutinous property was measured by adding water to the Protein-Sample to a 30% solids content, kneading the mixture to absorb water into the Sample uniformly, and observing the glutinous strength when the end of the pestle is removed from the bottom of the mortar. The larger the number of "+" symbols, the higher the glutinous property. The kneaded sample used in the glutinous property determination was then placed in a test tube which was then sealed, and the sample was heated at a temperature of 80° C for 30 minutes to determine the dispersibility in water. The heat-coagulating property was judged by observing the dispersibility. The addition of sucrose (5%) to the aqueous ammonia solution of proteins prior to the drying serves to prevent a denaturation of the proteins and to increase the water solubility of the proteins. Other saccharides such as lactose, glucose, xylose and the like or sugar alcohols such as inositol, mannitol and the like in an amount of about 2% can also be used for the same purpose in place of sucrose.

The microorganisms which can be employed in the present invention are yeasts such as *Candida utilis* (generally called as Tolula yeast), *Saccharmoyces cerevisiae*, *Saccharomyces carlsbergensis*, *Saccharomyces fragilis*, *Candida tropicalis*, *Candida lipolitica*, *Rodotrula glutinis* and the like, bacteria such as *Bacillus subtilis*, *Corynebacterium sp.* and the like, blue-green algae such as Arthorospira, Spiririna and the like, and green-algae such as *Chlorella vulgaris*, *Scenedesmus sp.* and the like.

In accordance with the method of this invention, it is desirable that the above microorganisms be treated as an aqueous slurry containing 2 to 32%, preferably 3 to 17%, most preferably 4 to 7%, of living cells on a dry basis. However, when the microorganisms tend to be autolyzed at a pH of 7 to 10.5 as described hereinafter in Example 2, it is preferred that the aqueous slurry contain 5 to 32% living cells on a dry basis.

As described previously, the microorganisms as an aqueous slurry are subjected to chemical treatment with an alkali, an acid or a hydrophilic solvent. The alkali treatment can be accomplished by autolyzing the microorganisms with an alkali, for example, ammonia, or hydroxides, carbonates, lactates, citrates, succinates and acetates of cations such as sodium, potassium, ammonium, magnesium, calcium and the like at a pH of from 7.0 to 10.5, preferably 7.5 to 9.5, at a temperature of 25° to 65° C for a period of from 16 hours to 10 minutes. For example, at a pH of from 7.5 to 8.5, the autolysis can be completed in 0.5 to 6 hours at 40° C or in 10 minutes to 3 hours at 60° C. When a pH of 7.5 to 9.5 is used in the autolysis, it is desirable to use a preservative such as ethyl acetate, toluene or the like in an amount of 0.5 to 3% by weight based on the weight of the slurry. The above autolysis does not result in the production of proteins having a low molecular weight, in which the nucleic acids are decomposed into those having a low molecular weight. It is surprising that the resulting extract is almost free from a bitter taste. The extract thus obtained can be used, optionally after it is treated with activated carbon, for producing a yeast extract which is useful as a seasoning, a nutrient or a growth promoting substance for microorganisms. Alternatively, the alkali treatment can be accomplished by using sodium hydroxide or potassium hydroxide at a pH of from 10.5 to 12.9 at a temperature below 30° C for a period of about 4 minutes to 6 hours. As is apparent to one skilled in the art, the lower the pH or the lower the temperature, the longer will be the period for treatment required. As a standard, the alkali treatment can be completed at a pH of from 11.5 to 12.7 at 20° C for 2 hours to 20 minutes.

The acid treatment can be conducted using inorganic acids such as hydrochloric acid, sulfuric acid, phosphoric acid, carbonic acid and the like or organic acids such as citric acid, lactic acid, acetic acid and the like at a pH of from 0.5 to 4.0 at a temperature below 70° C for a period of from 2 hours to 20 minutes. Preferably, the acid treatment can be conducted at a pH of 3 to 1.0 at a temperature of 40° to 50° C for a period of from 40 to 100 minutes.

The treatment with a hydrophilic solvent can be accomplished by using dipolar or monopolar organic solvents which are freely miscible with water. Suitable examples of the hydrophilic solvent are acetone, methanol, ethanol, propanol, isopropanol and the like. In this treatment, it is desirable to reduce the moisture content in the cells as quickly as possible, i.e, within several minutes at a low temperature, generally below 30° C to dehydrate the cells by reducing the intracellular moisture content to a degree of less than 30%. For example, since the dehydration proceeds exothermically when it is effected using ethanol, the dehydration is preferably conducted at a temperature below 20° C. When the dehydration is conducted slowly at a temperature higher than 30° C, the proteins tend to be denaturated thereby decreasing this solubility in water. The amount of the hydrophilic solvent is generally more than about 2.4 times the amount of the moisture content in the living cells. For example, a cell having a moisture content of 70% is advantageously dehydrated with a hydrophilic solvent in an amount of more than 164% (70% × 2.4). The amount of the solvent required for the dehydration can be reduced by, for example, dividing the total amount of the solvent into two or more equal portions and effecting the dehydration in 2 or more stages at a low temperature using a solid-liquid separations. It is preferred that the dehydration be conducted using a hydrophilic solvent in an amount of 4 or more times the volume of the moisture in the cells until the moisture content is reduced to less than 20%. After the moisture content is reduced to less than 30%, lipids can be extracted with at least one lipid extracting solvent such as an alcohol, for example, ethanol, isopropanol, butanol and the like, acetone, hexane, an ether or the like or a mixture thereof without adversely affecting the water solubility of the resulting proteins.

The chemically treated cells as described above can be directly subjected to the mechanical treatment, but, in order to purify the ruptured product it is preferred that the treated cells be immediately separated from the waste liquor (treating liquid) and the cell portion be washed thoroughly with water to remove the eluted nucleic acids or substances related thereto and lipids, etc.

The cells which have been chemically treated as described above can then be mechanically ruptured using an industrial wet-type disperser, i.e., Ottawa sand, or a ball mill using glass or ceramic beads, or zirconium or aluminum balls (hereinafter referred to "balls"), such as those available, i.e., the so-called sand grinder available from E. I. DuPont or a modified type thereof. The grain size suitable for use in the mechanical rupture of this invention is in the range of from 0.2 to 1.5 mm. Generally, Ottawa sand having a grain size of about 0.7 mm has been found to be effective but a grain size of about 0.5 mm can be effectively used for rupture of Chlorella and bacteria. However, from an economical standpoint, a grain size of from 0.5 to 2.5 mm is advantageously used in the mechanical rupture, and such balls can be a mixture of balls having different sizes. The balls are generally used in an amount of from 30 to 90% by volume relative to the volume of the vessel of the sand grinder. The sand grinder is preferably operated at a rate of from 400 m to 850 m per minute in terms of the peripheral speed of the disk mounted around the rotating axis of the grinder. When the grain size of the balls is in the range of 0.5 to 1.5 mm, the grinder is preferably rotated at a peripheral speed of from 550 to 700 m per minute.

When an alkaline yeast slurry is stirred in a sand grinder, the viscosity tends to increase and stable foams are formed during the rupturing thereby lowering the rupturing efficiency. Such foaming can be reduced by previously adjusting the pH of the slurry to 5 to 3 or less and using a vessel where the surface contacted with the slurry is resin coated or by adding ethyl alcohol to the slurry in an amount of 5 to 35%, preferably 5 to 30%, or by using a sand grinder of the slit separation type where the balls are separated by a slit in place of a sand grinder of an open screen separation type where the balls are separated by a screen. In the slit separation type grinder, the slurry treated in the grinder is discharged through an adjustable gap between the vessel and the top cover and is not brought into contact directly with air in the vessel thereby making it possible to avoid swallowing-up of air from the surface of the slurry.

A preferred method to be carried out for mechanically rupturing an alkaline microorganims slurry is to carry out the mechanical rupturing at a pH of 7 to 10.2. When an alkaline treated yeast slurry (pretreated at pH 10.5 to 12.9) is water washed, the pH of the slurry falls to about 7 to 10.2 due to loss of alkali in the water washing operation. Of course, pH may be adjusted to within the 7 to 10.2 pH range where needed prior to mechanical rupturing by addition of suitable alkali, such as sodium hydroxide or potassium hydroxide. It has been found that pH adjusted to 7 to 10.2 improves product quality and facilitates ease of handling of the ruptured cell product. In particular, a product of a relatively low viscosity range, say 8,000 to 15,000 cp. results from the mechanical rupturing step if the pH during mechanical rupturing is within the 7 to 10.2 pH range.

When the rupture is carried out continuously, the flow rate of the slurry per hour is preferably from about 40 times to about 1.8 times the volume of the vessel volume. The ruptured amount of cells per hour is preferably from an about 12 times to about 2 times the volume of the vessel volume. The temperature of the slurry during the rupture is preferably maintained at 0 to 50° C and can be controlled using a thermostatic means provided in the vessel jacket. Another suitable example of an apparatus for the rupturing is a high speed roll mill and an efficient rupturing in the high speed roll mill can be obtained with a slurry having a moisture contact of 45 to 65%. The adjustment of the moisture content can easily be effected by adding cells which have been dehydrated with a hydrophilic solvent or which have been subjected to a rapid drying at a cell temperature below 80° C using a spray dryer, or by adding a cereal flour such as corn flour, wheat flour, soybean four, potato flour and the like or a powder of wheat gluten, soybean protein, sodium alginate, starch and the like. The roll is generally rotated at a rate of 120 to 350 m per minute, preferably from about 130 to about 300 m per minute, in terms of the peripheral speed of the front roll under a roll pressure of about 20 Kg/cm$^2$ to 40 Kg/cm$^2$, preferably about 30 Kg/cm$^2$.

The treatment of the ruptured cells can be carried out using the following alternative procedures:

A. The slurry of the cells ruptured by the sand grinder as described above is adjusted to an alkaline pH, generally a pH of 8 to 11, to dissolve the exposed proteins at a temperature below 35° C. The mixture obtained as above is then subjected to treatment (1) or (2) below depending upon the type of the final product desired. That is (1) when a protein-rich product is desired, the mixture is centrifuged at an alkaline pH to separate the ruptured cell membrane and the supernatant is adjusted to the isoelectric point of the proteins, usually a pH of 4.5 to 3.5 to precipitate the proteins which are then collected using a suitable means. (2) When it is desired to merely eliminate the yeast odor, the above mixture is adjusted near the isoelectric point of the proteins, usually a pH of 3.5 to 4.5, and the precipitated proteins are collected using a suitable means together with the ruptured cell membrane. In particular, the cells which have previously been chemically treated at a pH of 7.0 to 10.5 are characterized by a less unpleasant odor. The precipitated proteins treated by (1) or (2) above are then washed with water and adjusted to a pH of from 4.8 to 6.2 with an alkali such as sodium hydroxide, ammonia and the like to produce a raw material for further processing. If a dried raw material is desired, spray drying can be employed efficiently on an industrial scale. When it is desirable to impart a free flowability to the dried slurry, the slurry can be adjusted to a pH higher than 6.5, preferably 6.5 to 8.5 with a volatile alkali, for example, ammonia and then spray dried while controlling the temperature of the air discharged at 120° C to 50° C, preferably 90° C to 60° C. When a product having an improved water solubility or dispersibility is desired a saccharide such as lactose, sucrose, glucose, maltose, xylose, fractose, arabinose dextrin and the like, a sugar ester, for example, esters of sucrose and fatty acids, a sugar alcohol, for example, inositol, xylitol, sorbitol, mannitol and the like, an edible polyphosphate which is allowed to be incorporated into foodstuffs, sodium alginate and the like can be dissolved in the slurry to be dried in an amount of 2 to 100%, generally 2 to 12%, by weight based on the dried solids content of the slurry and the resulting mixture can be dried at a temperature below 80° C, preferably below 70° to 40° C. The dried product can further be defatted at a relatively low temperature in order to obtain a product having a glutinous property.

B. The cells ruptured using a high speed three roll mill can be used advantageously as it is containing the ruptured cells or after addition of supplemental amino acids, in particlar methionine, etc. or after they are seasoned with a seasoning, for example, Kokubase BW Type available from Dai-Nippon Sugar Mfg. Co., Ltd., Japan and flavored for the production of processed foodstuffs such as artificial meats and the like. Also, the cells which have been subjected to the rupture of the cell membrane and mixed with wheat flour, corn flour and the like can be used as a raw material for breads, confections such as cookies, cakes, etc. In addition, a dried raw material for processing foodstuffs which are reinforced with nutrients can be obtained by granulating the ruptured cells using a granulator, flow-drying the granules at low temperatures and finally grinding the dried granules to obtain a powder. The drying procedure can also be applied to the cells ruptured by a sand grinder as described in (A) above by adjusting the water content of the ruptured cells to 20 to 40% by weight based on the dried solids content and adding or without adding saccharides as illustrated above, although the drying cost somewhat increases as compared with the drying procedure through the granulation described above.

The waste liquor from the treatment with an alkali or a hydrophilic solvent contains nucleic acids and substances related thereto, vitamins and other growth promoting factors for microorganisms and can be utilized in a culture medium for microorganisms. Further, since the waste liquor is generally free from a bitter taste and also free from a burning smell or a decomposition odor which is inherent in the protein obtained by the conventional alkali extraction method, it can be used as seasonings or nutrients by adjusting the waste liquor to a pH of 1.0 to 7.0 with at least one acid, for example, hydrochloric acid, phosphoric acid, carbonic acid (or carbon dioxide), acetic acid, lactic acid, tartaric acid, succinic acid, citric acid, etc. and drying the mixture as it is or after the mixture is concentrated. In this instance, the waste liquor from the treatment with ammonia of a hydrophilic solvent can be adjusted to a pH of 5.0 to 6.0 by merely concentrating the waste liquor. If it is desirable to remove the nuceleic acids or substances related thereto and the yeast odor, the waste liquor can be treated with activated carbon which is then removed to obtain a yeast extract useful as a seasoning. The recovered activated carbon as it is or the washings obtained in washing of the waste activated carbon for reactivation can be used as a fertilizer for plants to increase the yield of the plants such as rice and wheat.

The present invention is further illustrated by the following examples but they are not to be construed as limiting the scope of this invention. In the Examples, the percents are by weight unless otherwise indicated.

EXAMPLE 1

The cultured cells of *Saccharomyces cervisiae* obtained by aerobically culturing the microorganism in a nirogen-rich medium comprising waste molasses as a carbon source for 17 hours were washed with water and filtered using a filter press to obtain 32 Kg of a yeast cell cake having a water content of 69% by weight. Analysis of the completely dried cells showed 54.6% crude proteins, 4.8% crude fats and 8.3% nucleic acids. The above cell cake was then slurried in water to produce an aqueous slurry containing 10% by weight of yeast cells on a dry basis, and the slurry was adjusted to a pH of 12.4 with 5N sodium hydroxide and stirred at a temperature of 18° C for 40 minutes. The cells thus treated were then separated into alkali treated yeast cells and an alkali waste liquor by a skimming type centrifuge, and the separated yeast cells were washed twice with warm water (about 35° C) in a volume equal to that of the slurry to complete the alkali treatment. Analysis of the completely dried cells of the alkali treated yeast showed 55.9% crude proteins and 0.87% crude nucleic acid. The pH of the yeast cells was then adjusted to 4.0 with 5N hydrochloric acid to prevent excess foaming and fed into a 10 liter content sand grinder equipped with seven disks at a rate of 40 liter per hour. 5 liter of glass beads having a grain size of 0.8 to 1.2 mm was then added to the sand grinder and the grinder was operated at a disk peripheral speed of 630 m per minute while passing cold water through a vessel jacket to keep the cell temperature below 30° C. After the slurry was repeatedly recycled seven times into the sand grinder to ensure complete rupture of the cells (the rupture ratio counted microscopically was found to be 96%), a precipitate comprising ruptured yeast cell membrane and proteins was recovered using a skimming type centrifuge, washed twice with water and adjusted to a pH of 5.6 with 1N sodium hydroxide. 3650 g of sucrose was added to the precipitate which was then adjusted to a pH of 9.0 with an aqueous ammonia, and the mixture was passed through a sand grinder at a flow rate of 40 liter per hour to dissolve and disperse the precipitated proteins. The mixture was spray-dried using a hot air having an inlet temperature of 160° C and an outlet temperature of 70° C to obtain 6.7 Kg of a dried product. The dried product thus obtained was found to contain 62.7% crude proteins, 0.4% ammoniacal nitrogen, 0.6% nucleic acid and 4.2% crude ash and found to have good solubility and dispersibility in water and heat-coagulating property.

EXAMPLE 2

30 Kg (73% water content) of packed yeast cells of *Candida utilis* was obtained in the same manner as described in Example 1. Analysis of the absolutely dried cells obtained above showed 57.2% crude proteins, 10.7% crude nucleic acids and 3.8% crude fats. The packed cells were charged into a kneader and adjusted to a pH of 8.5 with a 10% aqueous ammonia. After addition of 1000 cc of ethyl acetate, the mixture was stirred at a pH of 7.8 to 8.5 for 1 hour at a temperature of 55° C and transferred to a reaction tank. The total volume of the mixture was adjusted to 130 liter with warm water at 40° C, and the resulting slurry was stirred at a temperature of 40° C for 2 hours, separated into yeast cells and an alkali waste liquor using a skimming type centrifuge. The yeast cells were washed twice with warm water. Analysis of the completely dried cells obtained above showed 61.2% crude proteins and 1.3% crude nucleic acids. The alkali-treated cells were then slurried with water to produce an aqueous slurry containing 5% dried cells, and the slurry was repeatedly recylced 10 times to a sand grinder in the same manner as described in Example 1 to complete the rupture of the cell membranes (the percent rupture observed microscopically was found to be 93%). The resulting ruptures yeast cell liquid was concentrated to a 20% solids content using a thin-film evaporator and 1 Kg of sucrose was dissolved therein. The mixture was then spray-dried under the same conditions as those used in Example 1 to obtain 7.2 Kg of a powdered product. Analysis of the resulting product showed 4.2% water content, 62.3% crude proteins, 1.2% nucleic acids and 0.12% ammoniacal nitrogen. Separately, the alkali waste liquor was also concentrated to a 17% solids content (pH 5.7) using a thin-film evaporator, and the concentrate was adjusted to a pH of 7.0 with 1N sodium hydroxide, concentrated again to a 37% solids content and finally spray-dried to obtain 3.2 Kg of a yeast extract having a low sodium chloride content. The yeast extract thus obtained was almost free from a bitter taste and a puckery taste and exhibited a good flavor. Thus, the product can be used as a seasoning and a nutrient or a growth promoting material for animals and plants.

EXAMPLE 3

To 30 Kg of a living yeast of *Candida utilis* was added 0.3N hydrochloric acid to adjust the pH to 2.0 and the mixture was kept at a temperature of 50° C for 1 hour to complete the acid treatment. The mixture was then adjusted to a pH value of 4.0 with 0.5N sodium hydroxide, and slurried in water to prepare an aqueous slurry containing 15% yeast cells on a dry basis. The slurry was then subjected to rupture using a sand grinder in the same manner as described in Example 1 and the rupture ratio was microscopically observed to be 87%.

EXAMPLE 4

To 10 g (71% water content) of a living Torula yeast was added 2.5 ml of 1N sodium hydroxide while thoroughly blending. After allowing the mixture to stand for 5 minutes at room temperature, 20 ml of water was added to the mixture followed by thorough stirring to complete the alkali treatment. Separately, 22.5 ml of water was added to 10 g of the same yeast to obtain a control. Each of the alkali treated yeast and the control yeast was then ruptured using a Brawn Cell Homogeniser for 5 minutes using glass beads having a grain size of about 0.5 each instance mm. Analysis of the released ratio of nitrogenous compounds in eachinstance showed 81% in the alkali treated yeast and 49% in the control.

EXAMPLE 5

100 ml of ethanol was slowly added to 10 g of a living Torula yeast while thoroughly comminuting the yeast in a mortar and the mixture was maintained at a temperature of 43° C for 20 minutes. The cells were then separated and dried, and 22.5 ml of water was added to the cells. The resulting slurry was then ruptured in a Brawn Cell Homgeniser for a period of 5 minutes and the rupture ratio was microscopically counted and found to average 72%.

EXAMPLE 6

100 cc of ethanol was added slowly to 10 g (75% water content) of living cells of *Bacillus megatherium* while thoroughly stirring, and the mixture was treated at a temperature of 40° C for 20 minutes. The cells were then separated and dried, and 20 ml of water was added to the dried cells. The resulting slurry was then adjusted to a pH of 7.0 with 1N sodium hydroxide to obtain ethanol-treated cells. Separately, a sample, as a control, was prepared by adding 10 g (75% water content) of living cells of *Bacillus magatherium* to 22.5 ml of water and treated using a Brawn Cell Homogenizer for 10 minutes in the same manner as described in Example 4. The nitrogenous materials in each of the ethanol-treated cells and the control cells, and the analytical value of the released ratio of nitrogenous compounds was found to be 71% in the ethanol-treated cells and 31% in the control cells.

EXAMPLE 7

A baker's yeast (*Saccharomyces cerevisiae*) was aerobically cultured in a culture medium containing waste molasses and a sufficient amount of a nitrogen source for 18 hours and, after removal of the culture liquid, the cells were washed thoroughly with water to obtain 42 Kg (72% water content) of a yeast cell cake. 10 g of the yeast cell cake thus obtained were then slurried in water to produce a slurry containing 10% cells on a dry basis, and the slurry was adjusted to a pH of 12.7 with 5N sodium hydroxide. The slurry was stirred at a temperature of 21° C for 30 minutes followed by allowing the mixture to stand and adjusting the mixture to a pH of 6.0 with 1N hydrochloric acid. The slurry thus treated was centrifuged using a skimming type centrifuge to collect the yeast cells and the cells were washed twice with warm water (about 35° C) in an amount equal to that of the previous slurry. 3 Kg of the resulting alkali-treated yeast cells (total amount, 6 Kg; 73% water content) was spray-dried in the same manner as described in Example 1, and to 800 g of the dried cells was added water in an amount sufficient to adjust the moisture content to 60%. The moistened cells were then experimentally subjected to rupture of the cell membrane in a three roll mill rotating at a front roll speed of 150 rpm with the ratios of rotation being 1 : 2.6 : 6.3 and roll pressure being 30 Kg per cm$^2$. Microscopic observation of the cells which had been passed through the roll mill four times showed no original cells of the yeast. 2 g of the above treated cells was then dispersed and dissolved in 10 cc of 0.1N sodium hydroxide and the nitrogenous compounds released extracellularly was determined and found to be 93%.

EXAMPLE 8

A 18% (on dry weight basis) aqueous slurry of a baker's yeast available from Oriental K.K., Japan was subjected to NaOH treatment under various conditions as set forth in Table 2 followed by washing once with water to obtain an about 10% aqueous slurry of the yeast, which was fed into a sand grinder and was subjected to rupturing at 15° C for 10 minutes to obtain ruptured samples. The rupture ratio was determined microscopically.

The results are shown in Table 2.

pH 12.0 followed by immediately rupturing without washing it with water, according to the method of Kalina et al U.S. Pat. No. 3,821,080, to obtain the same rupture ratio as in Table 2 with a pH value unchanged. After rupturing the sample was removed of proteins at isoelectric point thereof with the result that 78% of RNA (based on the total content) remained in the protein fraction, i.e., only 22% of RNA was extracted.

EXAMPLE 9

A 18% (on a dry basis) aqueous slurry of the same baker's yeast as employed in Example 8 was subjected to NaOH treatment at 25° C for 1 hour with adding such an amount OF NaOH that the pH of ruptured slurry indicates pH values as set forth in Table 2 below. The thus treated slurry was washed once with water and adjusted with respect to its water content to obtain an about 10% (based on a dry basis) aqueous slurry of the yeast, which was then ruptured at 15° C till the rupture ratio of the slurry reached at least 90%. The viscosity of the thus obtained sample was determined.

The resuls are shown in Table 3.

TABLE 3

| pH | 6.0 | 6.7 | 7.0 | 7.6 | 9.0 | 9.5 |
|---|---|---|---|---|---|---|
| Viscosity (cp) | 56,000 | 17,000 | 14,000 | 12,000 | 10,000 | 8,400 |
| pH | 9.8 | 10.0 | 10.2 | 10.6 | 12.0 | |
| Viscosity (cp) | 9,600 | 9,600 | 13,000 | 24,000 | 61,000 | |

From the results in Table 3, it is apparent that a pH range of 7 to 10.2 gave a relatively low range of viscosity, which was suited for handling.

It will be clear from the results in Table 2 that a ruptured slurry having the above range of pH was obtained by subjecting an aqueous slurry of the yeast to NaOH treatment at a pH range of 10.5 to 12.9 followed by washing with water and rupturing.

On the other hand, in accordance with the method of Kalina et al the sample which was directly subjected to rupturing after the alkali treatment gave a ruptured slurry only with a higher pH range and higher viscosity.

As is apparent from the results in Tables 2 and 3, a step of washing the slurry with water, after being subjected to NaOH treatment, can effectively lower the pH vaue of value slurry, which gives favorable effects on handling as well as the quality of the product.

While the invention has been described in detail and with reference to specific embodiments thereof, it will be apparent to one skilled in the art that various

TABLE 2

| | Conditions of NaOH Treatment | | | NaOH Treated Solution before Rupturing | | | |
|---|---|---|---|---|---|---|---|
| pH of Slurry | Amount of NaOH (g/100g dry yeast) | Temp. (° C) | Time (min.) | RNA Extracted (%) | Biuret Protein Remaining (%) | Rupture Ratio (%) | pH of Ruptured Slurry |
| 10.5 | Ca. 5 | 30 | 360 | 42 | 98 | 83 | 7.7 |
| 11.5 | Ca. 6 | 20 | 120 | 52 | 93 | 82 | 7.9 |
| 12.0 | Ca. 7 | 20 | 120 | 72 | 93 | 96 | 8.8 |
| 12.2 | Ca. 7.5 | 30 | 60 | 78 | 95 | 94 | 9.0 |
| 12.3 | Ca. 8.5 | 27 | 60 | 83 | 93 | 93 | 9.2 |
| 12.5 | Ca. 10 | 25 | 60 | 84 | 92 | 98 | 9.6 |
| 12.7 | Ca. 12 | 20 | 40 | 82 | 88 | 96 | 9.7 |
| 12.9 | Ca. 15 | 30 | 4 | 38 | 93 | 82 | 9.9 |
| 12.9 | Ca. 14.5 | 20 | 20 | 79 | 84 | 92 | 9.9 |
| 13.1 | Ca. 20 | 25 | 20 | 89 | 64 | 81 | 10.1 |

From the results in Table 2, it can be seen that in order to obtain 50% or more of RNA extracted and 80% or more of protein remaining a pH range of 10.5 to 12.9 was suited.

As a comparison experiment the same yeast sample as in Example 8 was subjected to NAOH treatment at changes and modifications can be made therein without departing from the spirit and scope thereof.

What is claimed is:

1. A method for treating a slurry of microorganisms which comprises
    1. chemically treating the microorganisms for at least about 4 minutes with at least one alkali selected from the group consisting of sodium hydroxide and potassium hydroxide at a pH of from 10.5 to 12.9 and at a temperature of from 0° C to 30° C to form a mixture of chemically treated microorganism cells and waste liquid,
    2. separating said microorganism cells from said waste liquid,
    3. washing the separated microorganism cells with water to remove eluted nucleic acids or substances related thereto and lipids,
    4. adding water to form a slurry of microorganism cells,
    5. mechanically rupturing the cell membranes of the resulting chemically treated microorganisms using a three roll mill, or a sand grinder of the slit separation type at a pH of 7 to 10.2.
2. The method of claim 1, wherein the pH of said slurry prior to mechanical rupturing is reduced to 7 to 10.2 solely through the washing step of step (3) in conjunction with addition of water of step (4) of claim 1.
3. The method of claim 1, wherein said mechanical rupturing is carried out using a three roll mill in the presence of 45 to 65 percent by weight of water based on the weight of the separated cells.
4. The method of claim 1, wherein the inner surface of the mill or grinder is resin coated.
5. The method of claim 1, wherein ethyl alcohol is added to the slurry prior to mechanical rupturing in an amount of 5 to 35%.
6. The method of claim 1, wherein a slit separation type said grinder is employed.
7. The method according to claim 1, wherein said microorganism is a yeast selected from the group consisting of *Candida utilis*, *Saccharomyces cerevisiae*, *Saccharmoyces fragilis*, *Saccharomyces carlsbergensis*, *Candida tropicalis*, *Candida lipolitica* and *Rodotorula glutinis*, a bacterium selected from the group consisting of *Bacillus subtilis* and *Corynebacterium sp.* or an algae selected from the group consisting of Arthrospira, Spirurina, *Chlorella vulgaris* and *Scenedesmus sp.*

* * * * *